United States Patent [19]

Nichols

[11] 4,245,637
[45] Jan. 20, 1981

[54] SHUTOFF VALVE SLEEVE

[76] Inventor: Robert L. Nichols, 808 Ft. Worth St., Jacksonville, Tex. 75766

[21] Appl. No.: 923,346

[22] Filed: Jul. 10, 1978

[51] Int. Cl.³ .............................................. A61M 1/00
[52] U.S. Cl. ................................... 128/276; 137/205; 128/274; 137/202;203;192;193
[58] Field of Search ............... 128/215, 2 F, 276, 277, 128/278, 275; 15/353; 55/216; 210/123, 124, 125, 126; 215/307; 137/202, 203, 192, 193

[56] References Cited

U.S. PATENT DOCUMENTS

| 2,161,097 | 6/1939 | Schröder-Nielsen | 215/307 |
|---|---|---|---|
| 3,605,786 | 9/1971 | Machin, Jr. | 137/205 |
| 3,646,935 | 3/1972 | Holbrook et al. | 128/276 |
| 3,648,698 | 3/1972 | Doherty | 128/276 |
| 3,685,517 | 8/1972 | Reynolds | 128/277 |
| 3,719,197 | 3/1973 | Pannier et al. | 137/205 |
| 3,805,788 | 4/1974 | Kleiner | 128/276 |
| 3,811,485 | 5/1974 | Holbrook | 137/205 |
| 3,960,165 | 6/1976 | Holbrook et al. | 128/276 |
| 3,965,902 | 6/1976 | Reilly et al. | 128/276 |
| 3,965,903 | 6/1976 | Cranage | 128/276 |
| 3,989,046 | 11/1976 | Pannier et al. | 128/276 |
| 3,993,067 | 11/1976 | Schachet | 128/276 |
| 4,013,076 | 3/1977 | Pauderbaugh et al. | 128/276 |
| 4,111,204 | 9/1978 | Hessel | 128/276 |

FOREIGN PATENT DOCUMENTS 665265 1/1963 Canada .................................. 15/353

Primary Examiner—Robert W. Michell
Assistant Examiner—J. L. Kruter
Attorney, Agent, or Firm—Richards, Harris & Medlock

[57] ABSTRACT

The specification discloses a medical suction apparatus including a canister for receiving and containing fluid and a lid for sealably covering the canister. A patient port and a vacuum port extend through the lid, and a vertically slidable overflow plunger is provided for selectively blocking the vacuum port. A plunger guide directs the plunger towards the vacuum port, and a float is attached to the bottom of the plunger. When the fluid within the canister is below a predetermined level, the plunger and the float are supported at their lowermost position. As the fluid level rises, the float causes the plunger to be moved upwardly to close the vacuum port. An outer sleeve downwardly depends from the lid and partially encompasses the float for providing a tortuous path for air and fluid through the vacuum port to prevent direct migration of aerosol droplets, fluid droplets and condensation through the vacuum port.

5 Claims, 3 Drawing Figures

U.S. Patent
Jan. 20, 1981
4,245,637
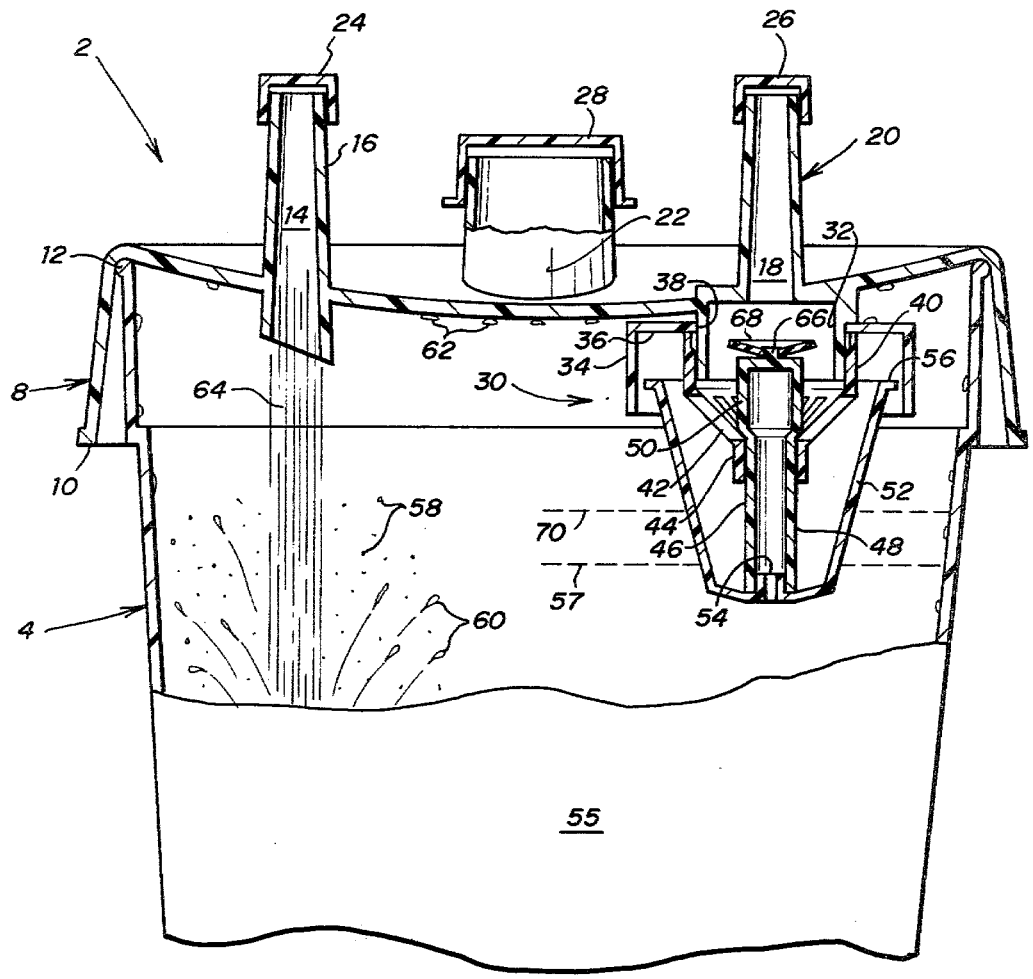
FIG. 1
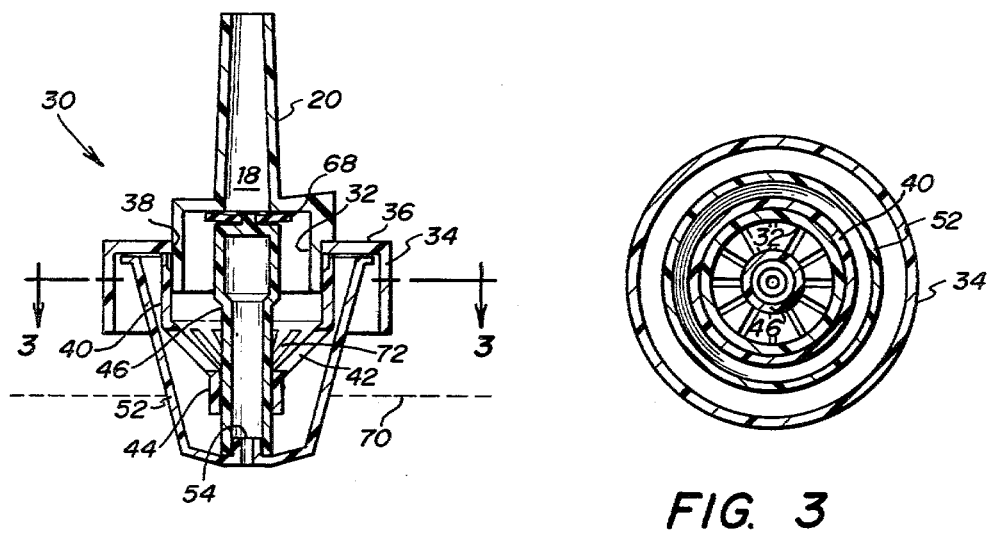
FIG. 2
FIG. 3

SHUTOFF VALVE SLEEVE

FIELD OF THE INVENTION

The present invention relates to medical suction apparatus and more particularly relates to a canister and lid assembly for use in a medical suction apparatus having structure for reducing the amount of fluid passing through the vacuum port in the lid.

BACKGROUND OF THE INVENTION

Medical suction apparatus have long been used in hospitals to remove fluids from a patient during various medical procedures. One type of apparatus commonly used to receive and contain fluid from a patient includes a canister covered by a lid, with a patient port and a vacuum port communicating through the lid. A tubular vacuum line is attached between a vacuum source and the vacuum port, and another tubular line is connected to the patient port for withdrawing fluid from the patient, through the patient port and into the canister. A shutoff valve is normally used to close or block the vacuum port when the fluid within the canister rises to a predetermined level, in order to prevent the patient fluid from entering and damaging or contaminating the hospital vacuum system.

In the use of conventional canister and lid assemblies in medical suction apparatus, certain quantities of fluid droplets have been heretofore drawn through the vacuum port. For example, when fluid enters the patient port and contacts the fluid in the bottom of the canister, aerosol and splash droplets are created. These droplets tend to move through the air in straight lines, and some droplets thus find their way to the exposed vacuum port in previously developed canister lids. Also, fluid condensation droplets often form on the underside of the canister lid. Such droplets often tend to migrate along the interior surface of the lid to the vicinity of the vacuum port, where they are aspirated into the vacuum port. Prior canister and lid assemblies have not been designed to prevent or reduce such migration of aerosol, splash or condensation droplets into the vacuum port, and thus, the vacuum equipment attached to prior canister vacuum ports has been damaged or fouled. Such damage has included not only the corrosion of such parts as regulators and diaphragms, but continued deposit of such fluid droplets has resulted in the constriction of vacuum passageways, and thus, reduction of vacuum flow. Moreover, the aspiration of patient fluids into a vacuum system can cause bacteriological contamination of the vacuum system, obviously an undesirable result in a hospital environment.

A need has thus arisen for a suction canister lid assembly which eliminates or substantially reduces the aspiration of fluid droplets into the vacuum system.

SUMMARY OF THE INVENTION

The present invention solves the foregoing and other problems long associated with medical suction apparatus through the provision of a canister and lid assembly with structure to prevent direct migration of fluid droplets into the vacuum port to reduce the amount of fluid entering the vacuum port to an acceptably low level.

In accordance with the present invention, a medical suction apparatus is provided including a canister for receiving and containing fluid. A lid sealably covers the canister, and a patient port and a vacuum port communicate between the interior and exterior of the canister covered by the lid. A shutoff valve is provided for blocking the vacuum port when the fluid within the canister rises to a predetermined level. Downwardly depending wall structure is associated with the shutoff valve for providing a tortuous path for air and fluid through the shutoff valve and the vacuum port to prevent direct migration of aerosol droplets, fluid droplets and condensation droplets through the vacuum port. In this manner, the amount of fluid entering the vacuum port is substantially reduced.

In accordance with another aspect of the present invention, a medical suction apparatus includes a canister for receiving and containing fluid. A lid sealably covers the canister, and a patient port and a vacuum port are provided, each extending through the lid. A plunger and plunger guide are disposed beneath the lid adjacent to the vacuum port, with the plunger guide directing the plunger towards the vacuum port. A float is attached to the plunger, and the plunger guide supports both the plunger and the float when the fluid within the canister is below a first predetermined level. An outer sleeve depends downwardly from the lid and partially encompasses the float for providing a tortuous path for air and fluid through the vacuum port to prevent direct migration of aerosol droplets, fluid droplets and condensation droplets through the vacuum port. As the fluid within the canister rises to a second predetermined level, the float forces the plunger upwardly to block the vacuum port.

In accordance with a more specific aspect of the invention, an inner cylinder extends downwardly from the lid and is disposed concentrically about the lower end of the vacuum port. The outer sleeve depends from the lid by means of a hub extending inwardly from the top of the outer sleeve and having a centered aperture for snugly fitting about the inner cylinder. A clamping sleeve is clamped on the inner cylinder below the hub and supports the hub and the outer sleeve on the inner cylinder. Also, fingers extend from the clamping sleeve for supporting the plunger guide. The plunger guide comprises a cylindrical sleeve, and the plunger includes a lower cylindrical portion dimensioned to slide through the plunger guide and an upper portion having a sufficiently large cross section to prevent the upper portion from passing through the plunger guide. A prong extends upwardly from the interior bottom surface of the float and is frictionally attached to the lower end of the plunger. In this manner, the upper portion rests on the plunger guide to vertically support the plunger and the float when the fluid in the canister is below a first predetermined level.

BRIEF DESCRIPTION OF THE DRAWINGS

The advantages and further aspects of the present invention will be readily appreciated by those of ordinary skill in the art as the same becomes better understood by reference to the following detailed description when considered in conjunction with the accompanying drawings in which:

FIG. 1 is a partial cross sectional view of a canister and lid assembly of the present invention showing a patient port, a vacuum port, a shutoff valve and an outer sleeve for preventing direct migration of fluid droplets into the vacuum port;

FIG. 2 is a cross sectional view of the canister and lid assembly illustrating the shutoff valve in a closed position blocking the vacuum port; and FIG. 3 is a top cross sectional view of the valve and vacuum port taken generally along section lines 3—3 as shown in FIG. 2.

DETAILED DESCRIPTION OF THE DRAWINGS

Referring now to the drawings in which like reference characters refer to like or similar parts throughout the several views, there is shown in FIG. 1 a canister and lid assembly 2 embodying the present invention. The canister and lid assembly 2 includes a canister 4 conventionally constructed from a suitable plastic for receiving and containing fluid and a plastic lid 6 for sealably covering the canister 4. The lid 6 includes a downwardly extending annular lip 8 that is canted at a slight outward angle for providing a circumference at its lower edge 10 that is slightly greater than the circumference of the canister 4 at its upper edge 12. The provision of the lip 8 enables the lid 6 to be easily fitted over the canister 4 and to be forced downwardly to form a tight seal with the canister.

A patient port 14 is formed through one side of the lid 6 and includes a tapered cylinder 16 extending upwardly from the top of the lid 6. The taper of the cylinder 16 allows the cylinder to be inserted into flexible tubular suction lines to form a seal. Likewise, a vacuum port 18 is provided through the lid 6 at a location spaced apart from the patient port 14. The vacuum port 18 also includes an upwardly extending tapered cylinder 20 for attachment to a vacuum line. The top of the lid 6 also includes a spout 22 for emptying fluids from the canister 4. Appropriately dimensioned caps 24, 26 and 28 are provided for removably covering and sealing the cylinders 16 and 20 and the spout 22, respectively.

In operation, a suction or vacuum line is placed on cylinder 20 to create a vacuum inside the canister 4. Vacuum is applied through the line from a conventional hospital vacuum system. The vacuum inside canister 4, in turn, creates a suction at the patient port 14. When a tubular suction line is attached between the cylinder 16 and a patient, the suction at port 14 will withdraw fluid from the patient and flow the fluid into the canister 4.

A shutoff valve and protective sleeve assembly 30 is associated with the vacuum port 18 and constitutes an important aspect of the present invention. Assembly 30 includes an inner cylinder 32 integrally formed on the underside of lid 6 and extending downwardly from the lid 6 in a concentric relationship with the lower end of the vacuum port 18. An outer sleeve 34 depends from the inner cylinder 32 by means of a hub 36 extending inwardly from the top of the outer sleeve 34. The hub 36 has a centered aperture 38 for snugly fitting over the inner cylinder 32, and a clamping sleeve 40 is clamped on the inner cylinder 32 below the hub 36 for supporting the hub 36 and outer sleeve 34 in the illustrated position.

A plurality of spaced apart fingers 42 extend downwardly and inwardly from the clamping sleeve 40, and a cylindrical plunger guide 44 is supported on the fingers 42. The plunger guide 44 is disposed in a generally vertical direction, and a plunger 46 is slidably mounted within the plunger guide 44. The plunger 46 includes a cylindrical lower portion 48 that is dimensioned to pass through and slide within the plunger guide 44 and includes an upper portion 50 that has a cross sectional width of sufficient area to prevent the upper portion 50 from passing through the plunger guide 44. Thus, the upper portion 50 may rest on the plunger guide 44. In this manner, the plunger 46 is supported by the plunger guide 44 and directed for vertical sliding motion towards the vacuum port 18.

A float 52 having a truncated conical outer configuration is removably attached to the lower end of plunger 46 by means of a prong 54. The prong 54 extends upwardly from the bottom of float 52 for insertion into the lower end of plunger 46 and is dimensioned to frictionally engage the interior surfaces of the plunger 46 with a force sufficient to support the float 52. The walls of the float 52 extend upwardly such that the top edge 56 of the float 52 is disposed within the outer sleeve 34. Thus, in the assembled form of the invention, the outer sleeve 34 extends downwardly past the top edge 56 of float 52 and partially encompasses the float 52.

The shutoff valve and sleeve assembly 30 is operable to selectively block the vacuum port 18 when the canister is filled with fluid. When the fluid 55 in the canister 4 is below a first predetermined level generally indicated by a dotted line 57, the float 52 and the plunger 46 are supported at their lowermost position by the plunger guide 44, and the vacuum port 18 is in communication with the interior of canister 4. When vacuum is applied to the vacuum port 18, air passes from the interior of canister 4 upwardly between the outer sleeve 34 and top edge 56 of the float 52, then downwardly along the interior walls of the float 52, through the spaces between the fingers 42, then upwardly within the cylinder 32 and through the vacuum port 18. In this manner, a tortuous path is provided for the passage of air and fluid between the interior of canister 4 and the vacuum port 18.

The provision of a tortuous path for the passage of air and fluids through vacuum port 18 is an important aspect of the present invention. As noted during normal operations, aerosol fluid particles 58, fluid droplets 60 and condensation droplets 62 are formed within canister 4. As fluid 64 enters the canister 4 through the patient port 14 and drops towards the bottom of the canister 4, the falling action generates the splash droplets 60 and the aerosol particles 58. Also, condensation droplets 62 will form along the interior surfaces of the canister and lid assembly 2. In this droplet filled environment within the canister 4, it is important to provide a tortuous path between the interior of canister 4 and the vacuum port 18 in order to prevent an unacceptably large amount of fluid particles from directly migrating into the vacuum port 18. As they pass along the tortuous path, the majority of airborne fluid particles 58 and fluid droplets 60 will be deposited on cylinder 32 and float 52 instead of entering the vacuum port 18. The migrating droplets 62 will be stopped by sleeve 34 from entering vacuum port 18.

When the fluid 55 within the canister 4 reaches the first predetermined level indicated by dotted line 57, the float 52 begins to rise, causing the plunger 46 to slide upwardly within the plunger guide 44 towards the vacuum port 18. A tab 66 extends from the top surface of the plunger 46, and a concave flexible disc 68 is mounted on the top of the plunger by means of the tab 66 with its concave surface facing the vacuum port 18. The concave surface of the disc 68 is dimensioned to cover the vacuum port.

As the fluid 55 within canister 4 rises to a second predetermined level generally indicated by dotted line 70, the plunger 46 is forced upwardly by the float 52 until the disc 68 engages the vacuum port 18. In this manner, the vacuum port 18 is shut off or blocked by the disc 68 such that a vacuum can no longer be maintained within the canister 4. Thus, fluid 64 will cease to enter the canister through the patient port 14.

Referring now to FIG. 2, a cross sectional view of the shutoff valve and sleeve assembly 30 is shown with the plunger 46 in position as it would appear when the fluid 55 within canister 4 has risen to the level generally indicated by dotted line 70. In this position, the circular disc 68 completely covers and blocks vacuum port 18. In this view, the plurality of openings or slots 72 are shown between the fingers 42. The vacuum port 18, when it is not blocked, communicates with the interior area of the canister and lid assembly 2 through the slots 72. It may be also seen in this view that the float 52 is slightly spaced apart from the hub 36 when the plunger 46 is in the raised position. Thus, the float 52 does not interfere with the sliding motion of the plunger 46.

Referring now to FIG. 3, a top cross sectional view of the shutoff valve and sleeve assembly 30 is shown taken generally through the line 3—3. In this view, the concentric and circular construction of the assembly 30 may be appreciated. Referring to FIGS. 2 and 3, the plunger 46 is cylindrical in shape and is located directly below port 18 in a coaxial or concentric relationship. Disposed outwardly and concentrically from the plunger 46 are the inner cylinder 32 and the clamping sleeve 40. The wall of float 52 is also disposed concentrically with respect to plunger 46 and is spaced apart in an outward direction from the clamping sleeve 40. Finally, the outer sleeve 34 is also concentrically disposed and partially encompasses float 52.

Thus, it will be appreciated that the present invention utilizes a shutoff valve and sleeve assembly 30 designed to provide a tortuous path between the vacuum port 18 and the interior of the canister and lid assembly 2. In this manner, direct migration of fluid droplets 60 into the vacuum port 18 is prevented.

Although a particular embodiment of the invention has been described in the foregoing detailed description, it will be understood that the invention is capable of numerous rearrangements, modifications and substitutions of parts without departing from the spirit of the invention.

What is claimed is:

1. A medical suction apparatus comprising in combination:
    a canister for receiving and containing fluid;
    a lid sealably covering said canister;
    a patient port extending through said lid for receiving fluid from a patient during medical suction procedures;
    a vacuum port extending through said lid and adapted for attachment to a suction line to create a vacuum inside said canister;
    a plunger movable for selectively blocking said vacuum port;
    a plunger guide directing said plunger for vertical sliding motion relative to said vacuum port;
    a float attached to said plunger, said plunger guide being operable to vertically support said plunger and float at a lower level when the fluid in said canister is below a first predetermined level, said float operable to cause said plunger to terminate the application of vacuum to said canister when fluid level arises to a predetermined level in said canister; and
    an outer sleeve downwardly depending from said lid and partially encompassing said float for providing a tortuous path for air and fluid through said shutoff valve and vacuum port to prevent direct migration of fluid particles through said vacuum port, and comprising:
    an inner cylinder depending downwardly from said lid and disposed concentrically about the lower end of said vacuum port;
    a hub extending inwardly from the top of said outer sleeve and having a center aperture for snugly fitting about said inner cylinder; and
    a clamping sleeve removably clamped on said inner cylinder for supporting said hub and outer sleeve on said inner cylinder.

2. The suction apparatus as set forth in claim 1 and further comprising fingers spaced apart by openings extending from said clamping sleeve for supporting said plunger guide, said outer sleeve and said float disposed between said openings and the fluid contained in said canister to prevent linear migration of fluid particles through said openings and said vacuum port.

3. A medical suction apparatus comprising in combination:
    a canister for receiving and containing fluid;
    a lid sealably covering said canister;
    a patient port extending through said lid for receiving fluid from a patient during medical suction procedures;
    a vacuum port extending through said lid and adapted for attachment to a suction line to create a vacuum inside said canister;
    a plunger movable for selectively blocking said vacuum port;
    a plunger guide directing said plunger for vertical sliding motion relative to said vacuum port;
    a float attached to said plunger, said plunger guide being operable to vertically support said plunger and float at a lower level when the fluid in said canister is below a first predetermined level, said float operable to cause said plunger to terminate the application of vacuum to said canister when fluid level rises to a predetermined level in said canister;
    a prong extending upwardly from the bottom of said float for frictional attachment to said plunger; and
    an outer sleeve downwardly depending from said lid and partially encompassing said float for providing a tortuous path for air and fluid through said shutoff valve and vacuum port to prevent direct migration of fluid particles through said vacuum port.

4. In medical suction apparatus including a canister for receiving and containing fluids, with a vacuum port communicating between the interior and exterior of said canister and a shutoff valve for blocking the vacuum port when the fluid within the canister rises to a predetermined level, the improvement in combination therewith comprising:
    wall structure associated with the shutoff valve comprising a plurality of spaced circumferential sleeves concentrically surrounding said vacuum port, said sleeves defining a serpentine radial flow path toward the vacuum port, and providing a tortuous path for air and fluid through the shutoff valve and vacuum port to prevent direct migration of fluid particles through the vacuum port, and
    a cup-like movable float having a upper annular rim and associated with the shutoff valve, and wherein said sleeves are closed on top and open downwardly and receive said upper annular rim of said float in an annular gap therebetween such that said tortuous path becomes more acutely constrained as said float rises in response to increasing fluid level in the canister.

5. The suction apparatus as set forth in claim 4 wherein said upper annular rim of said float moves vertically in the annular gap immediately incentrically adjacent the outermost of said concentric sleeves, said rim defining a first infection point in said tortuous path, this first inflection point becoming more acutely constrained as said float rises in response to increasing fluid level in said canister whereby to present an increasingly resistive entry barrier against the admission of fluid particles to the remainder of said tortuous path to said vacuum port.

* * * * *